United States Patent [19]

Greenspan et al.

[11] 3,930,952

[45] Jan. 6, 1976

[54] MICROBIOLOGICAL REDUCTION OF $PGA_2$ AND 15-EPI $PGA_2$

[75] Inventors: George Greenspan, Narberth, Pa.; Michael R. G. Leeming, Canterbury, England

[73] Assignee: American Home Products Corporation, New York, N.Y.

[22] Filed: Apr. 4, 1975

[21] Appl. No.: 565,034

Related U.S. Application Data

[63] Continuation of Ser. No. 420,407, Nov. 30, 1973, abandoned.

[52] U.S. Cl. ................................ 195/51 R; 195/30
[51] Int. Cl.² ........................................... C12D 1/02
[58] Field of Search ........................... 195/51 R, 30

[56] References Cited
UNITED STATES PATENTS 3,788,947   1/1974   Hsu et al. ........................ 195/51 R

*Primary Examiner*—Alvin E. Tanenholtz
*Attorney, Agent, or Firm*—Robert Wiser

[57] ABSTRACT

Reduction of 7(2-[(3R and 3S)-3-hydroxy-1-octenyl]-5-oxo-3-cyclopenten-1-yl)-5-heptenoic acid by microorganisms of the genera *Streptomyces, Pseudomonas* and *Corynebacterium* is disclosed. The products 7-(2-[(3R)-3-hydroxy-1-octenyl]-5-oxo-cyclopentyl)-5-heptenoic acid(11-deoxy-15-epi-$PGE_2$), which is novel, and 7-(2-[(3S)-3-hydroxy-1-octenyl]-5-oxo-3-cyclopentyl)-5-heptenoic acid(11-deoxy-$PGE_2$), respectively, are useful as intermediates for the synthesis of other physiologically active ingredients.

13 Claims, No Drawings

MICROBIOLOGICAL REDUCTION OF PGA$_2$ AND 15-EPI PGA$_2$

This is a continuation of application Ser. No. 420,407, filed Nov. 30, 1973, now abandoned.

BACKGROUND OF THE INVENTION

The present invention provides a method of directly converting ring unsaturated prostaglandins of the 15-epi PGA$_2$ and PGA$_2$ type, that is, 7-(2-[(3R and 3S)-3-hydroxy-1-octenyl]-5-oxo-3-cyclopenten-1-yl)-5-heptenoic acids, to 11-deoxy-15-epi- and 11-deoxy-PGE$_2$, respectively.

SUMMARY OF THE INVENTION

The invention sought to be patented in its principal process aspect is described as residing in the concept of a process for the preparation of 7-[2-(3-hydroxy-1-octenyl)-5-oxo-cyclopentyl]-5-heptenoic acid which comprises treating 7-[2-(3-hydroxy-1-octenyl)-5-oxo-cyclopenten-1-yl]-5-heptenoic acid, with an organism selected from the genera:
  a. *Streptomyces*,
  b. *Pseudomonas*, and
  c. *Corynebacterium*.

The tangible embodiments produced by the principal process aspect of the invention possess the inherent general physical properties of being oily liquids, being substantially insoluble in water, and generally soluble in such common organic solvents such as ethers, ketones, and esters, e.g., diethyl ether, acetone, and ethyl acetate.

Examination of the products produced by the aforesaid process reveals, upon infrared, ultraviolet, nuclear magnetic resonance, mass spectral, and thin layer chromatographic analyses, spectral data, and migration rates supporting the molecular structure hereinbefore set forth.

The tangible embodiments produced by the principal process aspect of the invention possess the inherent applied use characteristic of being an intermediate in the synthesis of other useful prostaglandins.

The invention sought to be patented in a first subgeneric process aspect is described as residing in the concept of a process for the preparation of 7-(2-[(3R)-3-hydroxy-1-octenyl]-5-oxo-cyclopentyl)-5-heptenoic acid which comprises treating 7-(2-[(3S)-3-hydroxy-1-octenyl]-5-oxo-3-cyclopenten-1-yl)-5-heptenoic acid; with an organism selected from the genera:
  a. *Streptomyces*, and
  b. *Pseudomonas*.

The invention sought to be patented in a second subgeneric process aspect is described as residing in the concept of a process for the preparation of 7-(2-[(3S)-3-hydroxy-1-octenyl]-5-oxo-cyclopentyl)-5-heptenoic acid which comprises treating 7-(2-[(3S)-3-hydroxy-1-octenyl]-5-oxo-3-cyclopenten-1-yl)-5-heptenoic acid; with an organism selected from the genera:
  a. *Corynebacterium*,
  b. *Pseudomonas*, and
  c. *Streptomyces*.

DESCRIPTION OF THE PREFERRED EMBODIMENTS

In the process of the present invention, to produce, for example 7-(2-[(3R)-3-hydroxy-1-octenyl]-5-oxo-cyclopentyl)-5-heptenoic acid (11-deoxy-15-epi PGE$_2$), 7-(2-[(3R)-3-hydroxy-1-octenyl]-5-oxo-3-cyclopenten-1-yl)-5-heptenoic acid is contacted with a suspension of mycelial cells of the organism *Streptomyces griseus* NRRL 3231 in a substantially aqueous fermentation medium. The temperature and incubation time are not critical, and one skilled in the art will recognize that variations thereof will merely affect the attainment of optimum yield. Preferably the incubation period may last from about 18 to about 24 hours, typically about 22 hours, while the temperature is preferably maintained from about room temperature to about 30°, typically 28°. The pH of the aqueous medium may vary from about 4 to about 8, and the fermentation is conveniently carried out with agitation. The isolation of 11-deoxy-15-epi PGE$_2$ may be accomplished by standard techniques, for example, partitioning of the reaction mixture with an immiscible solvent followed by column chromatography of the material extracted by the organic phase.

While the process of the invention has been illustrated above by the use of 7-(2-[(3R)-3-hydroxy-1-octenyl]-5-oxo-3-cyclopenten-1-yl)-5-heptenoic acid as the starting material and *Streptomyces griseus* NRRL 3231 as the organism accomplishing the reduction, the substitution of the other starting materials and/or organisms contemplated as equivalents within the scope of the invention will be obvious to one skilled in the art. Thus, for *Streptomyces griseus* NRRL 3231 one may, for example, substitute other *Streptomyces* organisms, such as:

| | |
|---|---|
| *Streptomyces caelestis* | NRRL 2418 |
| *Streptomyces viridifaciens* | NRRL B-1679 |
| *Streptomyces rimosus forma paromomycinus* | NRRL 2455 |
| *Streptomyces rimosus* | ATCC 10970 |
| *Streptomyces aureofaciens* | NRRL B-1287 |
| *Streptomyces bellus* | NRRL B-2575 |
| *Streptomyces chartreusis* | NRRL 2287 |
| *Streptomyces avellaneus* | ATCC 23730 |
| *Streptomyces erumpens* | ATCC 23266 |
| *Streptomyces aureus* | ATCC 3309 |
| *Streptomyces cellulosae* | ATCC 3313 |
| *Streptomyces lipmanii* | ATCC 3331 |
| *Streptomyces antibioticus* | ATCC 8663 |
| *Streptomyces halstedii* | NRRL B-1235 |
| *Streptomyces lavendulae* | NRRL B-2343 |
| *Streptomyces spectabilis* | NRRL 2792 |
| | NRRL 2794 |

*Pseudomonas* organisms, such as:

| | |
|---|---|
| *Pseudomonas taetrolens* | NRRL B-14 |
| *Pseudomonas ribicola* | NRRL B-859 |
| *Pseudomonas papaveris* | NRRL B-1640 |
| *Pseudomonas septica* | NRRL B-2081 |
| *Pseudomonas aeruginosa* | QM B-1468 |
| *Pseudomonas reptilivora* | NRRL B-6bs |
| *Pseudomonas cruciviae* | NRRL B-1021 |
| *Pseudomonas acidovorans* | NRRL B-802 |
| *Pseudomonas putrefaciens* | NRRL B-950 |
| *Pseudomonas desmolytica* | NRRL B-979 |
| *Pseudomonas sp.* | NRRL B-3266 |
| *Pseudomonas sp.* | NRRL B-3294 | and *Corynebacterium* organisms, such as:

| | |
|---|---|
| *Corynebacterium simplex* | ATCC 6946 |
| *Corynebacterium hoagii* | ATCC 7005 |
| *Corynebacterium equi* | IFO 3730 |
| *Corynebacterium mediolanum* | NCIB 7205 |
| *Corynebacterium sepedonicum* | IFO 12188 |
| *Corynebacterium lilium* | NRRL B-2243 | and, for example, one may substitute for 7-(2-[(3R)-3-hydroxy-1-octenyl]-5-oxo-3-cyclopenten-1-yl)-5-heptenoic acid, 7-(2-[(3S)-3-hydroxy-1-octenyl]-5-oxo-3-cyclopenten-1-yl)-5-heptenoic acid.

While not critical, for optimum yield, the composition of the nutrient medium employed may vary. Preferably, a yeast extract-dextrose medium or a corn steep liquor medium, such as are described hereinbelow are preferred.

The starting materials for the practice of the invention, namely the aforementioned 7-(2-[(3R and 3S)-3-hydroxy-1-octenyl]-5-oxo-3-cyclopenten-1-yl)-5-heptenoic acids are well-known in the literature. For example, 7-(2-[(3R)-3-hydroxy-1-octenyl]-5-oxo-3-cyclopenten-1-yl)-5-heptenoic acid methyl ester, acetate may be obtained from the coral *Plexaura homomalia* by a procedure as described by A. Weinheimer and R. Spraggins in *Tetrahedron Letters*, 59, 5185, (1969). The diester may be hydrolyzed to the free hydroxyl and carboxyl functions by a procedure as described by Leeming and Greenspan in U.S. Pat. No. 3,726,765, Apr. 10, 1973. This may be esterified by standard techniques to produce the methyl ester. The methyl ester may be racemized to produce 7-(2-[(3S)-3-hydroxy-1-octenyl]-5-oxo-3-cyclopenten-1-yl)-5-heptenoic acid methyl ester by a procedure described by Bundy et al. in *Annals of New York Academy of Science*, Vol. 180, *Prostaglandins*, p. 76. Hydrolysis of the methyl ester to the free carboxylic acid may be accomplished by standard techniques.

7-(2-[(3R and 3S)-3-Hydroxy-1-octenyl]-5-oxo-cyclopentyl)-5-heptenoic acids are useful, for example, as intermediates for the synthesis of other prostaglandins which are bronchodilators. A typical synthesis is described in pending application Ser. No. 383,007, filed July 26, 1973, and copending with this application. Therein 7-(2-[(3R)-3-hydroxy-1-octenyl]-5-oxo-cyclopentyl)-5-heptenoic acid is oxidized to 7-[3(3-oxo-1-octenyl)-5-oxo-cyclopentyl]-5-heptenoic acid and substituents introduced into the 3-oxo group on the octenyl side chain, and the various double bonds are selectively reduced. Among the products thereof are the previously known compounds 11-deoxy-15-methyl-dihydro-PGE$_1$ (U.S. Pat. No. 3,671,370, June 20, 1972). 7-(2-[(3S)-3-Hydroxy-1-octenyl]-3-oxo-cyclopentyl)-3-heptenoic acid obviously can be used interchangeably in the above described sequence of reactions.

The following examples further illustrate the best mode contemplated by the inventors for carrying out the invention:

EXAMPLE I 7-(2-[(3R)-3-Hydroxy-1-Octenyl)-3-Oxo-Cyclopentyl]-3-Heptenoic Acid A. Five agar slants of *Streptomyces griseus* NRRL 3231 are each washed with 3 ml. of distilled water, and the cell suspensions transferred to five 1-liter flasks containing 200 ml. of yeast extract-dextrose medium described in Example II A. for 24 hours. Mycelial transfers, 800 ml., are made to a 14 liter fermentor containing 8 liters of the following medium:

| | |
|---|---|
| Corn Steep Liquor | 5.0 g. |
| Dextrose | 20.0 g. |
| Peptone | 20.0 g. |
| Distilled Water | 10.00 ml. |

The medium is autoclaved for 20 sec. at 121°C.

After 24 hours of incubation at 28°, agitation 130 rpm., aeration 4 liter of air per min., 7-(2-[(3R)-3-hydroxy-1-octenyl]-5-oxo-3-cyclopenten-1-yl)-5-heptenoic acid, 16 g. diluted in 90 ml. of ethanol, is added to the fermentor. Incubation is continued under the same conditions for 16.3 hours, when the agitation is increased to 200 rpm. and the aeration to 6 liters of air per min. The fermentation is harvested 3.5 hours later.

The pH of the fermentation mixture is lowered to pH 4.5–5.0 and then filtered. The mycelium is washed with warm water, and then water wash and filtrate are combined. The combined filtrate is extracted with ether and the extract washed, dried and evaporated. Silica chromatography of the residue with 35% ethyl acetate in hexane gives the title product 10.6 g. I.R. analysis $\lambda_{max}^{film}$ 3.0 (shoulder) 3.45, 5.80, 7.1, 8.15, 8.7, 10.35$\mu$. NMR Analysis: Signals at $\delta$ = 7.55 (singlet 2 protons, OH), 6.60 (multiplet, 2 protons, 13 and 14H), 6.40 (multiplet, 2 proton, 2-, 5- and GH), 4.12 (multiplet, 1 proton, 15H) ppm. Mass spectral analysis:

Calc: M$^+$, m/e 336 M$^+$–18 m/e 318.2194
Found: M$^+$, m/e 336 M$^+$–18 m/e 318.2178.

B. The same product as that obtained in part A above is obtained by following a procedure similar to that outlined in part A and substituting for the organism *Streptomyces griseus* NRRL 3231, the following organisms:

| | |
|---|---|
| *Pseudomonas taetrolens* | NRRL B-14 |
| *Pseudomonas ribicola* | NRRL B-859 |
| *Pseudomonas papaveris* | NRRL B-1640 |
| *Pseudomonas septica* | NRRL B-2081 |
| *Pseudomonas sp.* | NRRL B-3266 |
| *Psuedomonas sp.* | NRRL B-3294 |

EXAMPLE II 7-(2-[(3S)-3-Hydroxy-1-Octenyl]-5-Oxo-Cyclopentyl)-5-Heptenoic Acid A. Two agar slants of *Corynebacterium simplex* ATCC 6946 are each washed with 5 ml. of a yeast extract-dextrose (1% each) solution, and 4.5 ml. of the cell suspensions are transferred to each of two 1-liter flasks containing 200 ml. of the same medium:

| | |
|---|---|
| Yeast extract | 1% |
| Dextrose | 1% |
| Distilled Water | 100 ml. |

Autoclaved 15 sec., 121° C.

The flasks are incubated at 28° for 24 hours on a rotary shaker, as in Example I A. Twenty ml. transfers are made to 12, 1-liter flasks containing 200 ml. of the same medium, and a 10 ml. transfer is made to a 500 ml. flask with 100 ml. of medium.

After 25 hours of growth, the pH of the flasks is adjusted to 6.7 with 5 N HCl. Forty mg. of 7-(2-[(3S)-3-hydroxy-1-octenyl]-5-oxo-3-cyclopenten-1-yl)-5-heptenoic acid diluted in 2 ml. of ethanol is added to each one liter flask, and 20 mg. in one ml. of ethanol is added to the single 500 ml. flask. The flasks are put under N$_2$ and incubated as above. Following 22.5 hours of shaking, the flasks are harvested. The mixture is filtered and the filtrate acidified with acetic acid and extracted with ether. After washing and drying, the filtrate is evaporated and the resulting residue chromatographed on silica. Elution with 40% ethyl acetate in hexane affords 0.42 g. of the title product. I.R. Analysis: $\lambda_{max}^{film}$ 3.0 (shoulder), 3.4, 5.7, 7.05, 8.1, 8.6, 10.3μ.

NMR Analysis: 6.78 (S, 2, OH), 5.68 (M, 2, 13 and 14-H), 5.35 (M, 2.5 and 6-H), 4.12 (M, 1, 15-H) ppm.
Mass Spectral Analysis: M$^+$ at m/e 336 (theory = 336).

B. The same product as that obtained in part A above is obtained by following a procedure similar to that outlined in part A, but substituting for the organism Corynebacterium simplex ATCC 6946 the following organisms:

| | |
|---|---|
| Corynebacterium hoagii | ATCC 7005 |
| Corynebacterium equi | IFO 3730 |
| Corynebacterium mediolanum | NCIB 7205 |
| Corynebacterium sepedonicum | IFO 12188 |
| Corynebacterium lilium | NRRL B-2243 |
| Pseudomonas papaveris | NRRL B-1640 |
| Psuedomonas septica | NRRL B-2081 |
| Pseudomonas aeruginosa | QM B-1468 |
| Pseudomonas reptilivora | NRRL B-6bs |
| Pseudomonas cruciviae | NRRL B-1021 |
| Pseudomonas acidovorans | NRRL B-802 |
| Pseudomonas putrefaciens | NRRL B-950 |
| Pseudomonas desmolytica | NRRL B-979 |
| Pseudomonas sp. | NRRL B-3266 |
| Pseudomonas sp. | NRRL B-3291 |
| Streptomyces caelestis | NRRL 2418 |
| Streptomyces viridifaciens | NRRL B-1679 |
| Streptomyces rimosas forma paromomycinus | NRRL 2455 |
| Streptomyces rimosus | ATCC 10970 |
| Streptomyces aureofaciens | NRRL B-1287 |
| Streptomyces bellus | NRRL B-2575 |
| Streptomyces chartreusis | NRRL 2287 |
| Streptomyces avellaneus | ATCC 23730 |
| Streptomyces erumpens | ATCC 23266 |
| Streptomyces aureus | ATCC 3309 |
| Streptomyces cellulosae | ATCC 3313 |
| Streptomyces lipmanii | ATCC 3331 |
| Streptomyces antibioticus | ATCC 8663 |
| Streptomyces halstedii | NRRL B-1235 |
| Streptomyces avendulae | NRRL B-2343 |
| Streptomyces spectabilis | NRRL 2792, NRRL 2794 |

We claim:

1. A process for the preparation of 7-[2-(3-hydroxy-1-octenyl)-5-oxo-cyclopentyl]-5-heptenoic acid which comprises subjecting 7-[2-(3-hydroxy-1-octenyl)-5-oxo-cyclopenten-1-yl]-5-heptenoic acid to the fermentative action of an organism selected from the genera:
    a. Streptomyces,
    b. Pseudomonas, and
    c. Corynebacterium;
and then isolating the prostaglandin product.

2. A process as described in claim 1 for the preparation of 7-(2-[(3R)-3-hydroxy-1-octenyl]-5-oxo-cyclopentyl)-5-heptenoic acid which comprises subjecting 7-(2-[(3R)-3-hydroxy-1-octenyl]-5-oxo-3-cyclopenten-1-yl)-5-heptenoic acid to the fermentative action of an organism selected from the genera:
    a. Streptomyces, and
    b. Pseudomonas.

3. A process as described in claim 2 wherein 7-(2-[(3R)-3-hydroxy-1-octenyl]-5-oxo-3-cyclopenten-1-yl)-5-heptenoic acid is subjected to the fermentative action of Streptomyces griseus.

4. A process as described in claim 2 wherein 7-(2-[(3R)-3-hydroxy-1-octenyl]-5-oxo-3-cyclopenten-1-yl)-5-heptenoic acid is subjected to the fermentative action of Streptomyces griseus NRRL 3231.

5. A process as described in claim 2 wherein 7-(2-[(3R)-3-hydroxy-1-octenyl]-oxo-3-cyclopenten-1-yl)-5-heptenoic acid is subjected to the fermentative action of an organism selected from the genus Pseudomonas.

6. A process as described in claim 2 wherein 7-(2-[(3R)-3-hydroxy-1-octenyl]-5-oxo-3-cyclopenten-1-yl)-5-heptenoic acid is subjected to the fermentative action of Pseudomonas taetrolens NRRL B-14; Pseudomonas ribicola NRRL B-859; Pseudomonas papaveris NRRL B-1640; Pseudomonas septica NRRL B-2081; Pseudomonas sp. NRRL B-3266; or Pseudomonas sp. NRRL B-3294.

7. A process as described in claim 1 for the preparation of 7-(2-[(3S)-3-hydroxy-1-octenyl]-5-oxo-cyclopentyl)-5-heptenoic acid which comprises subjecting 7-(2-[(3S)-3-hydroxy-1-octenyl]-5-oxo-3-cyclopenten-1-yl)-5-heptenoic acid; to the fermentative action of an organism selected from the genera:
    a. Corynebacterium,
    b. Pseudomonas, and
    c. Streptomyces.

8. A process as described in claim 7 wherein 7-(2-[(3S)-3-hydroxy-1-octenyl]-5-oxo-3-cyclopenten-1-yl)-5-heptenoic acid is subjected to the fermentative action of an organism of the genus Corynebacterium.

9. A process as described in claim 7 wherein 7-(2-[(3S)-3-hydroxy-1-octenyl]-5-oxo-3-cyclopenten-1-yl)-5-heptenoic acid is subjected to the fermentative action of Corynebacterium hoagii; Corynebacterium equi; Corynebacterium mediolanum; Corynebacterium sepedonicum; Corynebacterium lilium; or Corynebacterium simplex.

10. A process as described in claim 7 wherein 7-(2-[(3S)-3-hydroxy-1-octenyl]-5-oxo-3-cyclopenten-1-yl)-5-heptenoic acid is subjected to the fermentative action of an organism of the genus Pseudomonas.

11. A process as described in claim 7 wherein 7-(2-[(3S)-3-hydroxy-1-octenyl]-5-oxo-3-cyclopenten-1-yl)-5-heptenoic acid is subjected to the fermentative action of Pseudomonas papaveris NRRL B-1630; Pseudomonas septica NRRL B-2081; Pseudomonas aeruginosa QM B-1468; Pseudomonas reptilivora NRRL B-6bs; Pseudomonas cruciviae NRRL B-1021; Pseudomonas acidovorans NRRL B-802; Pseudomonas putrefaciens NRRL B-950; Pseudomonas desmolytica NRRL B-979; Pseudomonas sp. NRRL B-3266; or Pseudomonas sp. NRRL B-3294.

12. A process as described in claim 7 wherein 7-(2-[(3S)-3-hydroxy-1-octenyl]-5-oxo-3-cyclopenten-1-yl)-5-heptenoic acid is subjected to the fermentative action of an organism of the genus Streptomyces.

13. A process as described in claim 7 wherein 7-(2-[(3S)-3-hydroxy-1-octenyl]-5-oxo-3-cyclopenten-1-yl)-5-heptenoic acid is subjected to the fermentative action of Streptomyces caelestis; Streptomyces viridifaciens; Streptomyces rimosus forma paromomycinus; Streptomyces rimosus; Streptomyces aureofaciens; Streptomyces bellus; Streptomyces chartreusis; Streptomyces avellaneus; Streptomyces erumpens; Streptomyces aureus; Streptomyces cellulosae; Streptomyces lipmanii; Streptomyces antibioticus; Streptomyces halstedii; Streptomyces lavendulae; or Streptomyces spectabilis.

* * * * *